US005507995A

United States Patent [19]

Schweich, Jr. et al.

[11] Patent Number: 5,507,995
[45] Date of Patent: Apr. 16, 1996

[54] PROCESS FOR MAKING A CATHETER

[75] Inventors: Cyril J. Schweich, Jr., St. Paul; James R. Pray, New Hope; Brian J. Brown, Hanover, all of Minn.

[73] Assignee: Scimed Life Systems, Inc., Maple Grove, Minn.

[21] Appl. No.: 274,393

[22] Filed: Jul. 12, 1994

Related U.S. Application Data

[62] Division of Ser. No. 19,479, Feb. 18, 1993, Pat. No. 5,358,493.

[51] Int. Cl.⁶ ................................................. B29C 59/02
[52] U.S. Cl. .......................................... 264/293; 264/320
[58] Field of Search ........................................ 264/293, 320

[56] References Cited

U.S. PATENT DOCUMENTS

| | | |
|---|---|---|
| 2,437,542 | 3/1949 | Krippendorf . |
| 3,406,685 | 10/1968 | May . |
| 3,416,531 | 12/1968 | Edwards . |
| 3,605,750 | 9/1971 | Sheridan . |
| 3,618,614 | 11/1971 | Flynn . |
| 3,935,857 | 2/1976 | Co . |
| 3,965,909 | 6/1976 | Waddell et al. . |
| 4,117,836 | 10/1978 | Erikson . |
| 4,239,042 | 12/1980 | Asai . |
| 4,279,252 | 7/1981 | Martin . |
| 4,280,500 | 7/1981 | Ono . |
| 4,385,635 | 5/1983 | Ruiz . |
| 4,417,886 | 11/1983 | Frankhouser et al. . |
| 4,425,919 | 1/1984 | Alston . |
| 4,430,083 | 2/1984 | Ganz . |
| 4,437,857 | 3/1984 | Goldstein et al. . |
| 4,464,176 | 8/1984 | Wijayarathna . |
| 4,531,943 | 7/1985 | Van Tassel et al. . |
| 4,551,292 | 11/1985 | Fletcher et al. . |
| 4,563,181 | 1/1986 | Wijayarathna . |
| 4,573,476 | 3/1986 | Ruiz . |
| 4,581,390 | 4/1986 | Flynn . |
| 4,596,563 | 6/1986 | Pande . |
| 4,627,844 | 12/1986 | Schmitt . |
| 4,636,346 | 1/1987 | Gold et al. . |
| 4,639,252 | 1/1987 | Kelly et al. . |
| 4,661,094 | 4/1987 | Simpson . |
| 4,690,175 | 9/1987 | Ouchi . |
| 4,739,768 | 4/1988 | Engelson . |
| 4,775,371 | 10/1988 | Mueller, Jr. . |
| 4,817,613 | 4/1989 | Jaraczewski . |
| 4,842,590 | 6/1989 | Tanabe . |
| 4,863,442 | 9/1989 | Demello . |
| 4,886,506 | 12/1989 | Lovgren . |
| 4,898,591 | 2/1990 | Jang . |
| 4,899,787 | 2/1990 | Ouchi . |
| 4,920,980 | 5/1990 | Jackowski . |
| 4,955,862 | 9/1990 | Sepetka . |
| 4,960,410 | 10/1990 | Pinchuk . |
| 5,017,259 | 5/1991 | Kohsai . |
| 5,034,005 | 7/1991 | Appling . |
| 5,045,072 | 9/1991 | Castillo . |
| 5,047,045 | 9/1991 | Arney . |
| 5,061,257 | 10/1991 | Martinez . |
| 5,069,673 | 12/1991 | Shwab . |
| 5,078,702 | 1/1992 | Pomeranz . |
| 5,085,649 | 5/1992 | Flynn . |
| 5,116,652 | 5/1992 | Alzner . |
| 5,125,909 | 6/1992 | Heimberger . |
| 5,156,592 | 10/1992 | Martin . |
| 5,160,559 | 11/1992 | Scovil . |
| 5,184,627 | 2/1993 | De Toledo . |

FOREIGN PATENT DOCUMENTS

| | | |
|---|---|---|
| 0117093 | 8/1984 | European Pat. Off. . |
| 0127261 | 12/1984 | European Pat. Off. . |
| 0180348 | 5/1986 | European Pat. Off. . |
| 3531 | of 1913 | United Kingdom . |
| 2044109 | 10/1980 | United Kingdom . |
| WO84/04664 | 12/1984 | WIPO . |

OTHER PUBLICATIONS

Berenstein, "Brachiocephalic Vessel: Selective and Superselective Catheterization", Radiology 148, pp. 437–441 (1983).

Freeny, "Subselective Diagnostic and Interventional Arteriography Using a Simple Coaxial Catheter System", Cardiovascular Interventional Radiology, pp. 209–213 (1984).

Hospital Price List, USCI Division, C.R. Bard, Inc. (1985).

Direction Pamphlet For Rentrop Infusion Catheter, uSCI Division, C.R. Bard, Inc. (Undated).

*Primary Examiner*—Leo B. Tentoni
*Attorney, Agent, or Firm*—Willian Brinks Hofer Gilson & Lione

[57] ABSTRACT

An intravascular catheter for providing access to distal vascular sites. The intravascular catheter comprises an elongate shaft with a lumen extending therethrough. The elongate shaft is comprised of a composite construction and has a proximal relatively stiff section, a distal section relatively more flexible than the proximal section, and an intermediate section between the proximal and the distal sections that provides a transition in flexibility between the proximal section and the distal section. The distal section has surface contours that impart flexibility to the distal section. A method for processing a tubular member with surface contours for use in a medical device, such as a catheter or guide wire, is also provided.

21 Claims, 3 Drawing Sheets

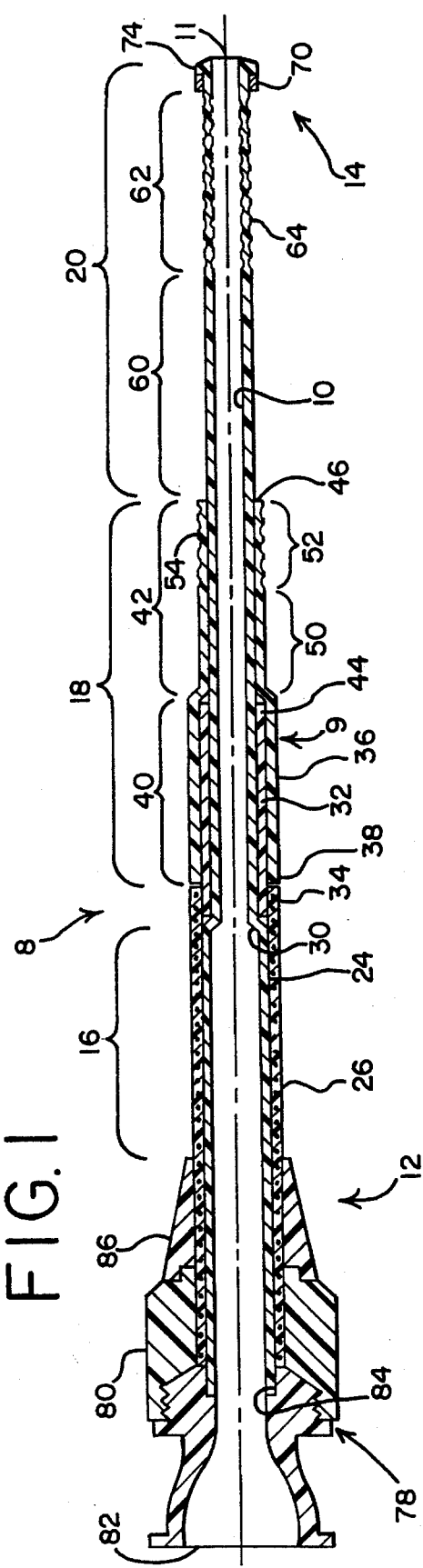
FIG. 1
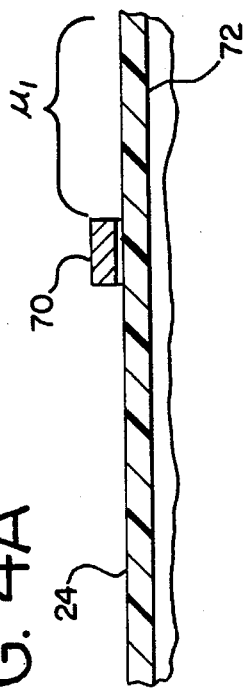
FIG. 4A
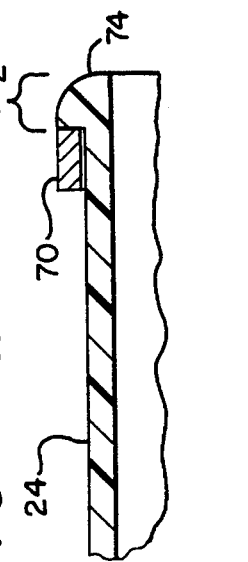
FIG. 4B
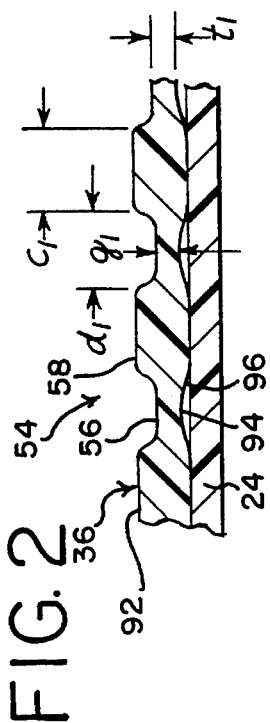
FIG. 2
FIG. 3

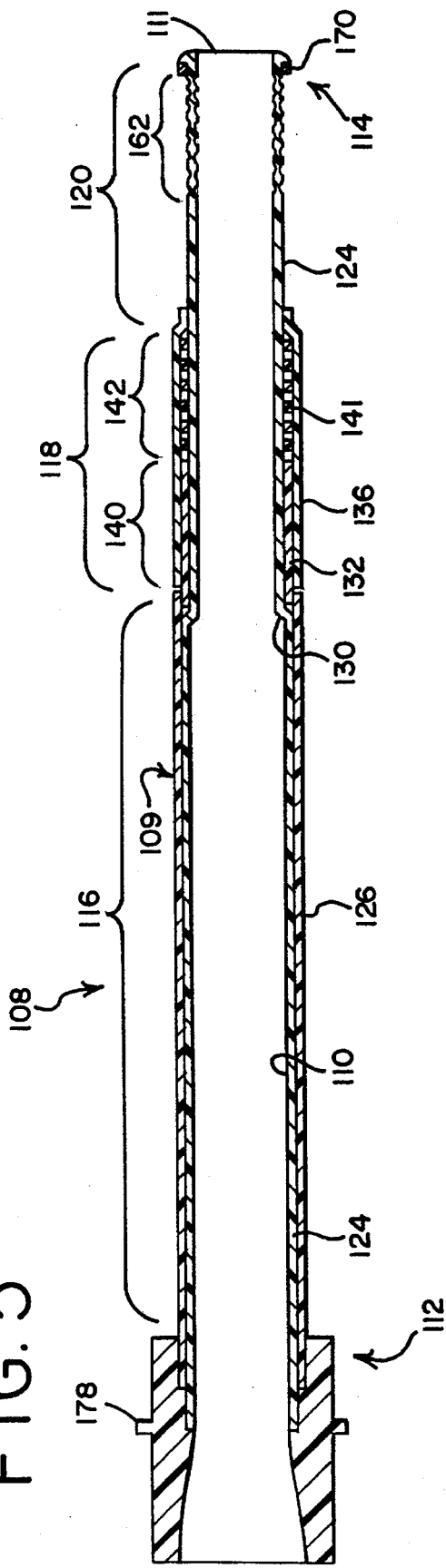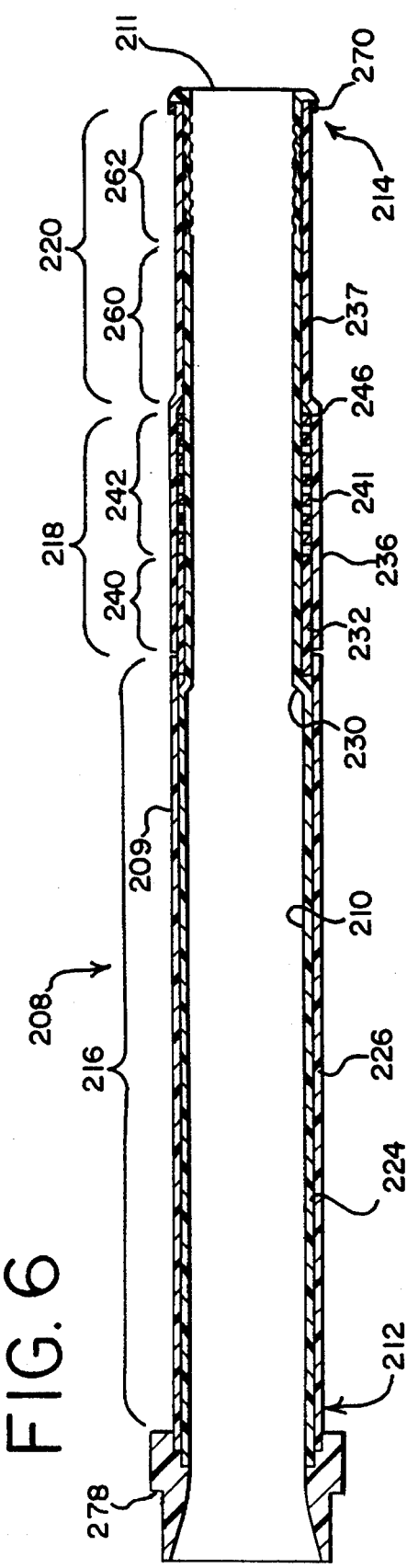

PROCESS FOR MAKING A CATHETER

This application is a division of Ser. No. 08/019,479, filed Feb. 18, 1993, now U.S. Pat. No. 5,358,493.

BACKGROUND OF THE INVENTION

The present invention relates to intravascular catheters, and more specifically the present invention relates to intravascular catheters for accessing difficult to reach regions of the human body such as the vasculature and methods for manufacture thereof.

Interventional procedures that rely on catheterization of a patient's vasculature have proven to be effective for diagnosis and treatment of various diseases and conditions. Interventional procedures for the coronary arteries, such as angiography and angioplasty, are by now routinely performed as needed. Procedures such as these are also useful in the peripheral vasculature. More recently, consideration has been directed to the further development of interventional procedures for other hard to reach vascular sites, such as the brain and liver. For example, it would facilitate diagnosis of certain conditions if radiopaque dye injections could be made to vascular sites deep within the brain. Also, there are procedures to repair an aneurysm in a vessel branch of the brain that involve infusing embolic material to seal off the vessel and/or lesion. Also, there are catheterization procedures for the treatment of arterial-venous malformations (AVM's) that include the infusion of embolic materials via a catheter. Other therapeutic infusions involve the use of coils, glue, collagens, ethanol, chemotherapy agents and thrombolytic agents, to name a few.

Accessing distal vascular sites such as deep within the brain via the arterial system poses unique difficulties. The arteries that lead to the brain, i.e. the carotid and vertebral arterial branches, are characterized by numerous and tortuous branchings. Subselective catheterization of higher order carotid arteries, (e.g. third, fourth, fifth or even higher), can be very difficult even for a highly skilled interventionalist. One of the factors that has made subselective catheterization of the carotid or vertebral arteries so difficult is the absence of a catheter suitable for subselective catheterization of higher order arterial branches.

A catheter suitable for access to remote vascular sites along tortuous vascular passages should possess certain features. For example, the catheter should track well over a guide wire. Another feature that is desirable in a vascular access catheter is pushability. Another desirable feature is a relatively large lumen size in order to infuse drugs, dye, agents, or other materials through the lumen even with a guide wire at least partially in place.

Accordingly, it is an object of the present invention to provide a catheter suitable for vascular access of high order vascular branches.

SUMMARY OF THE INVENTION

According to an aspect of the present invention, there is provided an intravascular catheter for providing access to distal vascular sites. The intravascular catheter comprises an elongate shaft with a lumen extending therethrough. The elongate shaft is comprised of a composite construction and has a proximal relatively stiff section, a distal section relatively more flexible than the proximal section, and an intermediate section between the proximal and the distal sections that provides a transition in flexibility between the proximal section and the distal section. The distal section has a surface contour that imparts flexibility to the distal section.

According to a further aspect of the invention, the vascular access catheter includes a composite construction in which an elongate shaft is formed of a plurality of tubular members. The tubular members are incorporated in sections of the elongate catheter shaft to provide favorable operating characteristics, and other features and advantages.

According to a yet further aspect of the invention, there is provided a method for manufacturing a tubular member to have favorable properties particularly useful in medical devices such as catheters and guide wires.

BRIEF DESCRIPTION OF THE DRAWINGS

FIG. 1 shows a longitudinal sectional view of a first embodiment of the present invention.

FIG. 2 shows an enlarged longitudinal sectional view of the tubular wall in an intermediate portion of the embodiment of FIG. 1.

FIG. 3 shows an enlarged longitudinal sectional view of the tubular wall in a distal portion of the embodiment of FIG. 1.

FIG. 4a shows a longitudinal cross section of the most distal end of the embodiment of FIG. 1 during a stage of manufacture.

FIG. 4b shows a view similar to that of FIG. 4a in a later stage of manufacture.

FIG. 5 shows a longitudinal sectional view of another embodiment of the present invention.

FIG. 6 shows a longitudinal sectional view of yet another embodiment of the present invention.

DETAILED DESCRIPTION OF THE PRESENTLY PREFERRED EMBODIMENTS

I. First Preferred Embodiment

Figure 8:
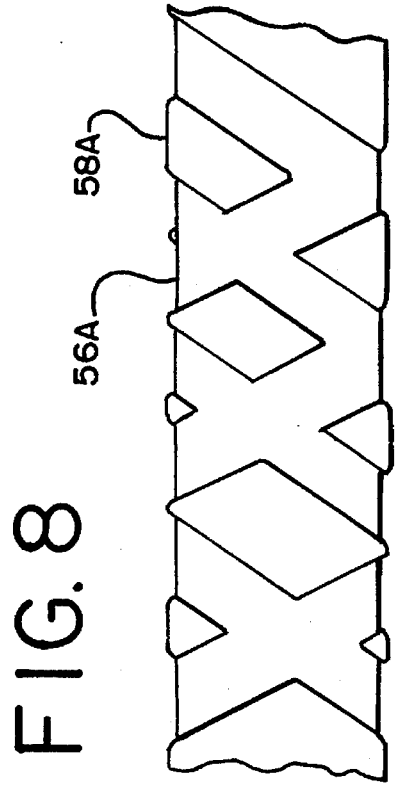
FIG. 8 is a side view of a portion of an alternative embodiment of the present invention.

Referring to FIG. 1, there is depicted a first preferred embodiment of the present invention. This embodiment is a vascular access catheter 8. The vascular access catheter 8 is intended for providing access to a distal site of the human vasculature. Such distal vascular sites may be in the coronary arteries, the carotid or vertebral arteries, or in peripheral arteries. Vascular locations that can be accessed may also be in tissue such as the brain or liver. The vascular access catheter is particularly suitable for subselectively accessing high order branches (e.g., third, fourth, fifth, or even higher order) of the human vasculature.

The vascular access catheter 8 includes a generally elongate shaft 9 with a lumen 10 that extends therethrough to a distal opening 11. The vascular access catheter 8 is preferably positioned into the subselective vascular sites over a guide wire that is received in the lumen 10. Conventional guide wires may be used with the vascular access catheter 8. A guide wire of 0.018 inch or smaller diameter is suitable for use with this embodiment. Other sizes of guide wires may be employed in alternative embodiments of the vascular access catheter provided in different sizes. The lumen 10 is also used for the delivery of fluids, such as drugs or dye, to the distal vascular site through the opening 11. The lumen 10 may also be used for infusion of embolic agents, aspiration, or other purposes.

In the first preferred embodiment, the elongate shaft 9 of the vascular access catheter 8 includes a proximal end 12 and a distal end 14. The catheter shaft 9 also includes several sections with properties, structure and features that provide for overall favorable handling and operating characteristics for subselective catheterization procedures. These sections include a proximal section 16, an intermediate section 18, and a distal section 20.

The proximal section 16 is a section of relatively uniform stiffness. The proximal section 16 is generally relatively more stiff than either the intermediate section 18 or the distal section 20. The intermediate section 18 is a section that undergoes a transition in flexibility and possesses increasingly greater flexibility going from the proximal to the distal direction. The increasing flexibility of the intermediate section 18 is not necessarily uniformly increasing although it is preferable to avoid abrupt transitions in flexibility. The intermediate section 18 is generally relatively less flexible overall than the distal section 20. The distal section 20 is a section of increasing flexibility in the distal direction at least in a portion of the distal section 20. Again, like the intermediate section 18, the distal section 20 need not be uniformly increasing in flexibility.

In this embodiment of the vascular access catheter 8, the favorable characteristics and properties are provided by means of a composite catheter construction, as follows: A first tubular member 24 extends from the proximal end 12 to the distal end 14. The first tubular member 24 defines the lumen 10 of the catheter 8. The first tubular member 24 is composed of a relatively hard plastic material, but with a relatively thin tubular wall. In this embodiment, the first tubular member 24 is composed of high density polyethylene (HDPE). A suitable HDPE is Marlex manufactured by Phillips Plastics. In the portion of the catheter 8 corresponding to the proximal section 16, the first tubular member 24 has a first size with uniform inner and outer diameters. In the proximal section 16, the first tubular member 24 has an inner diameter of 0.0235 inches and an outer diameter of 0.0295 inches, thereby providing a wall thickness of 0.003 inches.

Also, in the portion of the catheter 8 corresponding to the proximal section 16, a second tubular member 26 surrounds the first tubular member 24. The second tubular member 26 is relatively and uniformly stiff. The second tubular member 26 together with the inner tubular member 24 impart relative overall stiffness to the entire proximal section 16 compared to the intermediate section 18 and the distal section 20. In this embodiment, the second tubular member 26 is a composite tubing composed of a polyimide material with a braid of stainless steel imbedded therein. The polyimide braid composite tubing used for the second tubular member 26 is manufactured by HV Technologies of Trenton, Ga. The second tubular member 26 has an inner diameter of 0.0312 inches and an outer diameter of 0.038 inches, thereby providing a wall thickness of 0.0034 inches. The first and second tubular members 24 and 26 may be bonded together at their proximal or distal ends, or in a preferred embodiment, the first and second tubular members are bonded to other pieces in common, as explained in more detail below.

At a location 30 at which the first tubular member 24 goes from the proximal section 16 to the intermediate section 18, the first tubular member 24 undergoes a reduction to a second or reduced size. This reduction in size may be accomplished by a necking process or other suitable method. In the intermediate section 18, the first tubular member 24 has an inner diameter of 0.0215 inches and an outer diameter of 0.0270 inches, thereby providing a wall thickness of 0.0027 inches. In a preferred embodiment, the transition in size of the first tubular member 24 from the first size in the proximal section 16 to the second size in the intermediate section 18 possess a slight taper 30 so as to facilitate advancement of a guide wire across the transition, for example. The location at which the first tubular member 24 undergoes the transition in size occurs approximately 104 cm from the proximal end.

At a location immediately distal of where the first tubular member 24 necks down to the second or reduced size, a third tubular member 32 surrounds the first tubular member 24. The third tubular member 32 is composed of a relatively stiff, but thin walled material. The third tubular member 32 preferably has a uniform flexibility and uniform inner and outer diameters. In a preferred embodiment, the third tubular member 32 is composed of polyimide tubing having an outer diameter of 0.0308 inches and an inner diameter of 0.0278 inches, thereby providing a wall thickness of 0.0015 inches. Polyimide tubing suitable for the third tubular member is manufactured by HV Technologies of Trenton, Ga. The second tubular member 26 extends approximately 1 cm distally past the location 30 at which the first tubular member 24 necks down. Thus, a distal end 34 of the second tubular member 26 extends over the third tubular member 32 and overlaps it for approximately 1 cm. This overlapping provides strength to the composite construction of the elongate shaft 9 as well as provides a transition in flexibility from the proximal section 16 to the intermediate section 18. The third tubular member 32 is approximately 11 cm in length. The distal end 34 of the second tubular member 26 is bonded to the third tubular member 32 with an adhesive. Also, a portion of the first tubular member 24 immediately distal of the transition location 30 is bonded to the third tubular member 32 with an adhesive. A suitable adhesive for both these bonds is a urethane adhesive from HB Fuller.

The intermediate section 18 also includes a fourth tubular member 36. The fourth tubular member 36 surrounds the third tubular member 32. The fourth tubular member 36 is distal of the second tubular member 26. Specifically, a proximal end 38 of the fourth tubular member 36 is immediately adjacent to the distal end 34 of the second tubular member 26. The fourth tubular member 36 is made of a material that is relatively stiff yet is relatively more flexible than the second tubular member 26. Thus, the third tubular member 32, which underlies both the second tubular member 26 and the fourth tubular member 36, provides a transition in flexibility between them. The proximal end of the fourth tubular member 36 is bonded to the third tubular member 32 with a suitable adhesive such as a urethane adhesive from HB Fuller.

The fourth tubular member 36 is approximately 20 cm in length. Thus, a proximal region 40 of the fourth tubular member 36 having a length of approximately 10 cm surrounds the third tubular member 32 and a distal region 42 of the fourth tubular member 36 also having a length of approximately 10 cm extends distally beyond a distal end 44 of the third tubular member 32. The distal region 42 of the fourth tubular member 36 immediately surrounds the first tubular member 24. Therefore, the fourth tubular member 36 undergoes a transition in dimension from a first size to a second or reduced size between the proximal and distal regions 40 and 42. In a preferred embodiment, the proximal region 40 of the fourth tubular member 36 has an inner diameter of 0.0315 inches and an outer diameter of 0.0370 inches, thereby providing a wall thickness of 0.0027 inches. The distal region 42 of the fourth tubular member 36 has an inner diameter of 0.0280 inches and an outer diameter of 0.0330 inches, thereby providing a wall thickness of 0.0025 inches. The distal end 46 of the fourth tubular member 36 is bonded to the first tubular member 24 with an adhesive. A suitable adhesive is a urethane adhesive from HB Fuller.

The distal region 42 of the fourth tubular member 36 includes two segments. A proximal segment 50 of the distal region 42 has a uniform flexibility and a smooth outer surface. A distal segment 52 of the distal region 42 has contours 54 on the outer surface that impart greater flexibility to the distal segment 52 relative to the proximal segment 50 of the distal region 42. The proximal segment 50 and the distal segment 52 have approximately the same length, i.e., 5 cm. The surface contours 54 on the distal segment 52 are depicted in FIG. 2. The surface contours 54 represent a processing that reforms, removes, or compresses alternating annular or spiral portions of the material of the fourth tubular member 36. A preferred processing to form these surface contours is explained in detail below.

As shown in FIG. 2, processing of the distal segment 52 of the fourth tubular member 36 results in an alternating series of depressions or grooves 56 and ridges 58. The thickness, $t_1$, of the wall of the fourth tubular member 36 in the portion of the distal segment 52 corresponding to the ridges 58 represents the original wall thickness of the distal region, e.g. 0.0027. The depressions 56 formed in the distal segment 52 have a depth of approximately 0.0014 inches, so that the wall thickness, $g_1$, of the fourth tubular member 36 in the portion corresponding to the depressions in the distal segment 52 is approximately 0.0013. The portions of the contours 54 corresponding to the ridges 58 have a length, $c_1$, of approximately 0.004 inches. The portions of the contours 54 corresponding to the depressions 56 have a length, $d_1$, of approximately 0.003 inches. Accordingly, the contours have a peak-to-peak dimension of 0.007 inches. In a preferred embodiment, the contours 54 are formed by wedging or compressing the fourth tubular member 36 with a blunt implement while rotating the tubular member and advancing the implement thereby causing a spiral or annular-like depression to be formed in the distal segment 52. Alternatively, an annular depression could be formed.

In the distal section 20, the first tubular member 24 extends from the end 46 of the fourth tubular member 36 to the distal end 14 of the catheter 8. In the distal section 20, the first tubular member 24 has a first region 60 of relatively uniform flexibility that extends from the distal end 46 of the fourth tubular member 36. The outer surface of the first tubular member 24 in the first region 60 is smooth. The first region 60 has a length of approximately 15 cm. Within the distal section 20, adjacent to and distal of the first region 60 is a second region 62 of the first tubular member 24. In the second region 62, the first tubular member 24 is more flexible than in the first region 60. This flexibility is provided in the distal second region 62 by surface contours 64 on the first tubular member 24 that impart greater flexibility to the second region 62 relative to the first region 60. The second region 62 has a length of approximately 20 cm. The surface contours 64 on the second region 62 are depicted in FIG. 3. The surface contours 64 are formed by processing that reforms, removes, or compresses alternating annular or spiral portions of the material of the first tubular member 24 in this region. As shown in FIG. 3, processing of the second region 62 of the first tubular member 24 results in an alternating series of depressions or grooves 66 and ridges 68.

The thickness, $t_2$, of the wall of the first tubular member 24 in the region corresponding to the ridges 68 represents the original wall thickness of the first tubular member 24 in the distal section, i.e. 0.00275 inches. The depressions 66 formed in the second region 62 have a depth of approximately 0.0014 inches, so that the wall thickness, $g_2$, of the first tubular member 24 in the region corresponding to the depressions 66 in the second region 62 is approximately 0.0014 inches. The portions of the contours 64 corresponding to the ridges 68 have a length, $d_2$, of approximately 0.004 inches. The portions of the contours 64 corresponding to the depressions 66 have a length, $c_2$, of approximately 0.003 inches. Accordingly, the contours 64 have a peak-to-peak dimension of approximately 0.007 inches. In a preferred embodiment, the contours 64 are formed in the same manner as the contours 54 on the fourth tubular member 36, e.g. by wedging with a blunt implement. Also, like the contours 54 on the fourth tubular member 36, the contours 64 may be formed in the shape of annular depressions.

At the distal end 14 of the elongate shaft 9 is a marker 70. The marker 70 is composed of a metallic ring or band of a radiopaque material that can be observed fluoroscopically. The marker 70 may be made of 90% platinum/10% Iridium. In a present embodiment, the marker 70 has an outer diameter of 0.0317 inches, an inner diameter of 0.0277 inches and a length of 0.030 inches. The marker 70 may be bonded to the first tubular member 24 at the distal end 14 of the distal section 20. One presently preferred way of bonding the marker 70 onto the shaft 9 is to provide the first tubular member 24 in an unformed tip length, $u_1$, slightly greater than the desired finished tip length, as shown in FIG. 4A. Next, the marker 70 is slid over the unformed distal end 72 of the first tubular member 24 to approximately the desired position. Then, the unformed distal end 72 of the first tubular member 24 is heated and pressed in a proximal direction so that it fills in against the distal side of the marker band 70, forming a tip of finished length, $u_2$, as shown in FIG. 4B. This reformation of the distal tip of the first tubular member 24 provides for a suitable rounded tip 74 for the distal end 14 of the catheter 8 and also provides for securing the marker 70 from accidentally slipping off the distal end 14 of the elongate shaft 9.

The vascular access catheter 8 includes a manifold 78 located at and connected to the proximal end 12 of the elongate shaft 9. The manifold 78 includes a manifold body 80 with a port 82 and a bore 84. The bore 84 extends through the manifold body 80 communicating with both the lumen 10 of the elongate shaft 9 as well as the port 82. Approximately 0.5 cm of the proximal end 12 of the elongate shaft 9 extends into the bore 84 of the manifold body 80. In the present embodiment, the manifold 78 is bonded to the elongate shaft 9 and in particular to both the first tubular member 24 and the second tubular member 26. A suitable adhesive is a urethane adhesive manufactured by 3M Corp. The manifold body 80 is preferably made of a relatively hard plastic material such as polycarbonate. In a present embodiment, the manifold 78 is formed of a two-piece construction although a single piece construction would be suitable as well.

Located on a distal end of the manifold 78 and extending along the proximal end of the elongate shaft 9 is a strain relief 86. The strain relief 86 is made of a relatively flexible plastic material. In a preferred embodiment, the strain relief is made of synthetic rubber. A suitable synthetic rubber is Kraton, manufactured by Shell Chemical.

II. Methods of Operation

According to a method of operation, the vascular access catheter 8 is inserted percutaneously using conventional techniques and ancillary equipment, such as an introducer, a guide wire, and possibly a guide catheter. According to one method of use, an incision is made at a location at which the arterial system is readily accessible. Such a location may be a location at the groin where the femoral artery can be accessed. Another location is at the arm where the brachial artery may be accessed. The guide wire is positioned in the lumen of the vascular access catheter and the guide wire and the vascular access catheter may be advanced together from the incision location to the distal vessel site. If the incision location is relatively far from the distal vessel site, a guide catheter may be used. The distal tip of the guide wire may be extended out the distal end of the vascular access catheter to facilitate positioning. At locations where the arterial system branches, the distal end of the guide wire can be advanced into the desired branch. Injections of radiopaque dye may be used to observe vessel branchings. The radiopaque dye may be injected through the lumen of the vascular access catheter. Several orders of branches can be accessed in this manner.

Because the proximal section of the vascular access catheter is relatively stiff, the vascular access catheter can be readily pushed over the guide wire. The distal section of the vascular access catheter, because of its flexibility, can readily follow over the guide wire into high order branches. Moreover, due to the transitions in flexibility, such as those provided by the intermediate section, the vascular access catheter will not tend to kink or divert the guide wire from the desired path.

Of course, an individual's anatomy and the skill of the physician will be factors that affect the size and order of the vessels that can be accessed. However, the embodiments of the vascular access catheter provide advantages that allow for easier and improved access or access to portions of the vasculature that were beyond the reach of previous catheters.

As mentioned above, dye injections may be made with the vascular access catheter. The dye injections may be performed with the guide wire withdrawn entirely from the lumen of the vascular access catheter. Alternatively, dye injections may be made with the guide wire in place. This is due in part to the relatively large lumen provided by the vascular access catheter that allows a relatively large annular region around the guide wire to allow dye or other fluids such as medication to be injected through the lumen around the guide wire. The vascular access catheter has a relatively large lumen combined with a small size outer profile necessary to access vascular sites because of the use of thin walled high strength material for the tubular wall. Further, dye injections may be made with the guide wire partially withdrawn into the lumen.

III. Manufacturing Process to Impart Desired Flexibility Characteristics

As explained above, the distal segment 52 of the fourth tubular member 36 and the distal region 62 of the first tubular member 24 have surface contours, 54 and 64 respectively, that impart greater flexibility to these portions relative to adjacent portions that do not have contours. The contours provide for greater flexibility by reducing the cross sectional area of the walls of the tubular members 24 and 36 in areas corresponding to the depressions, 56 and 66 respectively.

The formation of the surface contours may be accomplished in a number of different ways. For example, the surface contours may be formed in the tubular member during the manufacture of the tube. This may be done by periodically narrowing a die through which the tube stock is being extruded or by molding the tube to form surface contours. Alternatively, the contours may be provided by a scoring process applied to a straight tubular member that actually removes a portion of the wall material of the tubular member in the area corresponding to the depressions. However, in a most preferred embodiment, the contours are formed by a process that removes little or none of the wall material of the tubular member as explained below.

Figure 7:
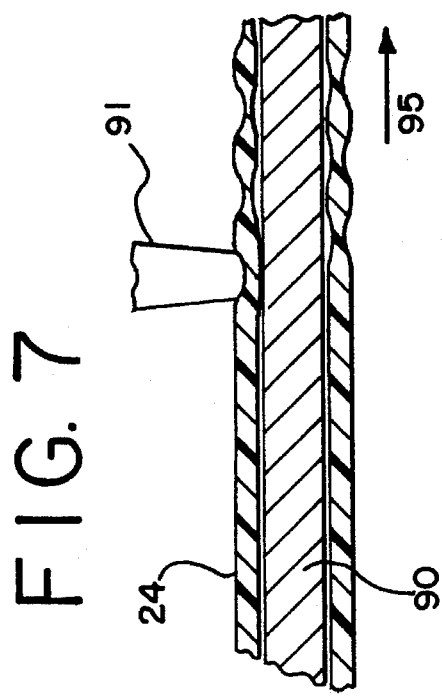
FIG. 7 depicts a manufacturing method for an intravascular device, such as the embodiments of FIGS. 1–6 and 8.

Referring to FIG. 7, according to the preferred process, a mandrel 90 is inserted into the tubular member 36. The size of the mandrel should be selected so that it occupies the lumen of the tubular member being processed. Accordingly, different size mandrels may be needed for different sizes of tubular members.

A blunt implement 91 is brought into engagement with the tubular member. Instead of a blunt implement, a blunt roller or a tensioned wire could be used. The blunt implement 91 has a dimension corresponding generally to that of the depression to be formed in the wall of the tubular member. In the present embodiment, the blunt implement is a blunt blade approximately 0.003 inches in width. It is preferred that the implement compresses the material of the tubular member rather than scores or cuts it. In the present embodiment, the blunt implement applies a compressive force of 150 gm on the tubular member to form the depression.

While the compressive force is being applied by the blunt implement to the tubular member, the tubular member is rotated relative to the implement while also being advanced axially relative to the implement in the direction of arrow 95 or vice versa, thereby forming the annular-like, or spiral, depressions in the tubular member.

In a preferred embodiment, the compressive reformation process may be performed at room temperature, i.e. cold worked. Alternatively, heat may be applied to facilitate the reformation process.

As can be observed from FIG. 2 the formation of grooves or depressions on an outer or first surface 92 of a tubular member may also result in a depression 94 on the opposite, i.e. inner, surface 96 at a location corresponding to the depression 56 on the outer surface 92. The depressions on the opposite or inner surface may be of a lesser depth than the depressions on the outer surface.

The preferred process described above is used to make a spiral depression in the tubular wall to form annular-like regions of compressively reformed material in the tubular wall separated by regions in which the material of the tubular wall is not reformed. According to the preferred embodiment, these regions are approximately of similar size to impart the desired flexibility characteristics. Alternatively, the size or pitch of the spiral depressions can be made larger or smaller to provide different characteristics. For example, by changing the pitch of the spiral depressions from close turns to more widely spaced turns, a transition in flexibility may be obtained. In further alternatives, the spiral depressions may have a right-handed or left-handed direction, or even a further embodiment may have both right-handed and left-handed spiral depressions 56A overlaid leaving areas 58A not reformed as shown in FIG. 8.

The processing of a thin-walled tubular member by formation of annular, or annular-like, compressively reformed regions is advantageously utilized in a vascular access catheter, as described above. The compressive reformation process to form annular depressed regions can also be used in other types of intravascular devices such as other types of catheters, like balloon dilation catheters, guide wires, guide catheters, introducers, and so on.

The above described process has a number of significant advantages. The above described process imparts greater bending flexibility and resistance to kinking to the tubular member along the region having the annular-like depressions. By compressively reforming the material of the catheter, the strength of the material is substantially retained. By comparison, if the material were cut or scored, the tubular member would possibly have reduced strength. Thus, desirable properties, such as hoop strength, column strength, compression strength, burst strength, tensile strength, and pushability, are retained while flexibility and resistance to kinking are substantially increased. Through the use of the compressive reformation process, a high strength tubular material can be used that has the same bending flexibility as a material of much lower strength.

In a preferred embodiment, the formation of annular compressed regions is used with high strength plastic materials, such as HDPE, polyester or polyimide, in order to take advantage of the high strength of such materials. The process could also advantageously be used with lower strength materials or thick-walled materials.

IV. A Second Preferred Embodiment

Referring to FIG. 5, there is a second embodiment of the present invention. A vascular access catheter 108 is shown having an elongate shaft 109 with a lumen 110 therethrough, and a proximal end 112 and a distal end 114. As in the first preferred embodiment, this embodiment of the vascular access catheter 108 has a proximal section, 116, an intermediate section 118, and a distal section 120. Also as in the first embodiment, the elongate shaft 109 is formed of a composite construction to provide the proximal section 116 with relative stiffness, the intermediate section 118 with increasing flexibility, and the distal section 120 with further flexibility.

The composite construction of the second embodiment includes a first tubular member 124 that extends from a proximal end 112 to the distal end 114 of the elongate shaft 109. The first tubular member 124 may be provided in a relatively hard plastic material but having a thin wall, such as HDPE in dimensions as in the first embodiment. Also, the first tubular member 124 undergoes a transition in size at a location 130 going from the proximal section 116 to the intermediate section 118. A second tubular member 126 formed of a relatively hard material, such as a composite material of polyimide with an embedded stainless steel braid, surrounds the first tubular member 124 in the proximal section 116.

In the intermediate section 118, the composite construction of the elongate shaft 109 of the second embodiment differs from that of the first embodiment. In the intermediate section 118, distal of the location 130 at which the first tubular member 124 undergoes a reduction in size, a third tubular member 132 surrounds the first tubular member 124. The third tubular member 132 extends along a proximal region 140 of the intermediate section 118. Distal of the third tubular member 132 and also surrounding the first tubular member 124 is a coil member 141. The coil member 141 extends over and surrounds the first tubular member 124 in a distal region 142 of the intermediate section 118. As in the first embodiment, a fourth tubular member 136 surrounds the third tubular member 132 in the proximal region 140 of the intermediate section 118. However, instead of undergoing a reduction in size and immediately surrounding the first tubular member 124 in the distal region 142 of the intermediate section 118, the fourth tubular member 136 continues over and surrounds the coil member 141. The distal end of the fourth tubular member 136 extends over the distal end of the coil member 141 and is bonded to the first tubular member 124 at the distal end of the intermediate section 118. Also, in this embodiment, the fourth tubular member 136 has a smooth outer surface along its entire length and is not provided with surface contours in a distal region thereof, as in the first embodiment.

The function of the surface contours in the first embodiment is provided instead by the coil member 141 in this second embodiment. In a preferred embodiment, the coil member 141 is composed of a polyimide coil. In one construction, the polyimide coil may be provided of the same piece of polyimide tubing used for the third tubular member 132. A distal portion of the tubing used for the third tubular member 132 is cut through the tubing wall into a spiral to form the polyimide coil which remains attached at a proximal end to the third tubular member 132. In alternative embodiments, the coil member may be composed of other materials such as other plastics or even metals.

The distal section 120 of the elongate shaft 109 of the vascular access catheter 108 of the present embodiment may be constructed similar to the first embodiment described above. The first tubular member 124 in the distal section 120 includes surface contours 164 in a distal region 162. Also, a marker 170 is located on the distal end 114 of the elongate shaft 109. A manifold 178 is located on the proximal end 112 of the elongate shaft 109.

V. A Third Preferred Embodiment

Referring to FIG. 6, there is depicted another embodiment of the vascular access catheter. This embodiment of a vascular access catheter 208 includes an elongate shaft 209 with a lumen 210 therethrough, and a proximal end 212 and a distal end 214. As in the previously described embodiments, this third embodiment of the vascular access catheter 208 has a proximal section 216, an intermediate section 218, and a distal section 220. Also, as in the two previous embodiments, the elongate shaft 209 is formed of a composite construction to provide the proximal section 216 with relative stiffness, the intermediate section 218 with increasing flexibility, and the distal section 220 with further flexibility.

The composite construction of the third embodiment includes a first tubular member 224 that extends from the proximal end 212 to the distal end 214 of the elongate shaft 209. The first tubular member 224 of this embodiment may be provided in the same materials as the first and second embodiments. Also, the first tubular member 224 undergoes a transition in size at a location 230 going from the proximal section 216 to the intermediate section 218. A second tubular member 226 formed of a relatively hard material, such as a composite material of polyimide with an embedded stainless steel braid, surrounds the first tubular member 224 in the proximal section 216.

In the intermediate section 218, the composite construction of the elongate shaft 209 of the third embodiment is similar to that of the second embodiment. In the intermediate section 218, distal of the location 230 at which the first tubular member 224 undergoes a reduction in size, a third tubular member 232 surrounds the first tubular member 224. The third tubular member 232 extends along a proximal region 240 of the intermediate section 218. Similar to the second embodiment described above, distal of the third tubular member 232 and also surrounding the first tubular member 224 is a coil member 241. The coil member 241 extends over and surrounds the first tubular member 224 in a distal region 242 of the intermediate section 218. As in the first and second embodiments, a fourth tubular member 236 surrounds the third tubular member 232 in the proximal region 240 of the intermediate section 218 and like the second embodiment, does not undergo a reduction in size in a distal region 242 of the intermediate section 228. The fourth tubular member 236 continues over and surrounds the coil member 241. The distal end of the fourth tubular member 236 extends over the distal end of the coil member 241. Also, in this third embodiment, the fourth tubular member 236 has a smooth outer surface along its entire length and is not provided with surface corrugations in a distal region thereof. In a preferred embodiment, the coil member 241 is composed of a polyimide coil.

This embodiment of the vascular access catheter 208 differs from the second embodiment in the distal section 220. In the distal section 220 of the elongate shaft 209 of the present embodiment, a portion 237 of the fourth tubular member 236 continues beyond the distal end 246 of the intermediate section 218 and surrounds the first tubular member 224 over the entire length of the distal section 220. Thus, unlike the first and second embodiments described above, in the third embodiment, the distal section 220 also possesses a composite construction of more than one tubular member. Also, in this embodiment, in a distal region 262 of the distal section 220, the first tubular member 224 includes surface contours 264 to impart greater flexibility to the distal region 262 of the distal section 220 relative to the proximal region 260. In this embodiment, the surface contours 262 may be provided from the interior surface of the first tubular member 224.

As in the previously described embodiments, a marker 270 is located on the distal end 214 of the elongate shaft 209. The marker 270 may be located between the layers that form the distal section 220, i.e., the first tubular member 224 and the distal portion 237 of the fourth tubular member 236. A manifold 278 is located on the proximal end of the elongate shaft 209.

VI. A Medical Guide Wire Embodiment

Figure 9:
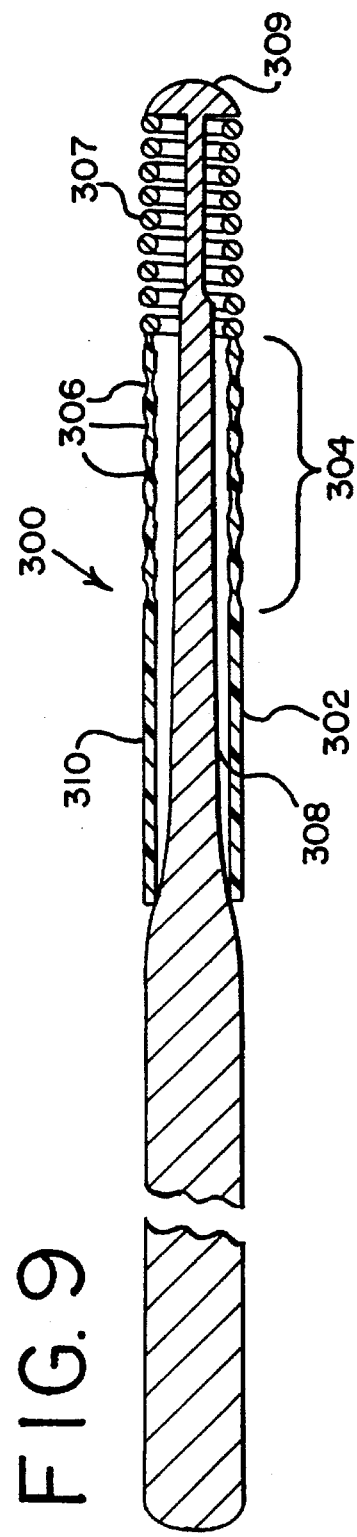
FIG. 9 is a longitudinal sectional view of a medical guide wire embodiment of the present invention.

Referring to FIG. 9, there is depicted another embodiment of the present invention. FIG. 9 shows a medical guide wire 300. Medical guide wires are used in various parts of the body, such as the vasculature, biliary tract, reproductive tract, urinary tract and gastro-intestinal system. Desirable characteristics in a medical guide wire include high strength and flexibility. The embodiment of the guide wire 300 shown in FIG. 9 provides these characteristics. The guide wire 300 includes a tubular member 302. The tubular member 302 includes a length 304 with a series of regions 306 in which the tubular member 302 has been compressively reformed. The compressive reformation process may be identical or similar to the process(es) described above in connection with the formation of the wall of the vascular access catheter embodiments. The guide Wire 300 may optionally also include a spring tip 306, a core 307, a blunt tip 309, and a tubular portion 310 that has not been compressively reformed.

VII. Further Alternative Embodiments

In the preferred embodiments of the vascular access catheter, the advantageous flexibility characteristics of the proximal, intermediate and distal sections including the preferred transitions in flexibility are provided by use of a composite construction of tubular members that are not tapered. In alternative embodiments, the advantageous flexibility characteristics may be provided with tubular members that possess tapers or changes in dimensions or even in a non-composite tubular member.

As mentioned above, the vascular access catheter has particular advantages for use in catheterization of the carotid and vertebral arteries. Alternatively, the present invention could be incorporated into catheters designed for other parts of the vasculature—both arterial and venous—and in the coronary and other peripheral vessels. Further, embodiments of the present invention could be incorporated into medical devices, such as catheters and guide wires, for other parts of the human body such as the biliary tract, the urinary tract, the gastro-intestinal tract, the reproductive system, and the endotracheal system.

It is intended that the foregoing detailed description be regarded as illustrated rather than limiting and that it is understood that the following claims including all equivalents are intended to define the scope of the invention.

We claim:

1. A method for forming a tubular member for a medical device comprising the steps of:

providing a tubular member of a plastic material, said tubular member having a wall with a surface and a length, and applying a compressive force to one side of the wall of the tubular member at a region of the tubular member along said length, said compressive force being sufficient to reform said material of said tubular member to impart a contour to said surface.

2. The method of claim 1 in which the step of applying a compressive force is further characterized by the step of:

applying a compressive force to an annular region of said tubular member.

3. The method of claim 1 in which the step of applying a compressive force is further characterized by the step of:

applying a compressive force to a series of annular regions of said tubular member.

4. The method of claim 1 in which the step of applying a compressive force is further characterized by the step of:

applying a compressive force to a spiral region of the wall of the tubular member to form an annular-like contour to said surface.

5. The method of claim 1 in which the step of applying a compressive force is further characterized by the step of:

applying a compressive force to the wall of the tubular member to form an annular-like contour to said surface, said contour comprised of annular-like regions in which the material of the tubular member is compressively reformed said regions being spaced apart from each other along the length of the tubular member.

6. The method of claim 1 in which said tubular member includes a lumen defined by said wall and further comprising the step of:

inserting a mandrel into said lumen prior to applying said force

7. The method of claim 1 in which said surface comprises an outer surface of the wall of said tubular member, said wall of said tubular member also having an inner surface, and further in which the step of applying a force is further characterized as applying a compressive force sufficient to impart a contour on both said inner surface and said outer surface.

8. The method of claim 1 in which the step of applying the compressive force is performed with a blunt implement that applies a force of 150 gm.

9. The method of claim 1 in which the step of applying a compressive force is carried out to only a portion of the length of the tubular member to provide a second region adjacent to the region to which the compressive force is applied such that the second region has an even surface.

10. The method of claim 1 in which the step of applying a compressive force is carried out with a blunt implement.

11. The method of claim 1 wherein the compressive force applied to one side of the wall of the tubular member is opposed by a force on an opposite side of the wall of the tubular member.

12. A method for forming a tubular member for a medical device comprising the steps of:

provoiding a tubular member of a plastic material, said tubular member having a wall with an inner surface, an outer surface and a length; and applying a compressive force to the outer surface of the wall of the tubular member at a region of the tubular member along said length, said compressive force being sufficient to reform said material of said tubular member to impart a contour to said surface.

13. The method of claim 12 in which the step of applying a compressive force is further characterized by the step of:

applying a compressive force to an annular region of said tubular member.

14. The method of claim 12 in which the step of applying a compressive force is further characterized by the step of:

applying a compressive force to a series of annular regions of said tubular member.

15. The method of claim 12 in which the step of applying a compressive force is further characterized by the step of:

applying a compressive force to a spiral region of the wall of the tubular member to form an annular-like contour to said surface.

16. The method of claim 12 in which the step of applying a compressive force is further characterized by the step of:

applying a compressive force to the wall of the tubular member to form an annular-like contour to said surface, said contour comprised of annular-like regions in which the material of the tubular member is compressively reformed said regions being spaced apart from each other along the length of the tubular member.

17. The method of claim 12 in which said tubular member includes a lumen defined by said wall and further comprising the step of:

inserting a mandrel into said lumen prior to applying said force.

18. The method of claim 12 in which said surface comprises an outer surface of the wall of said tubular member, said wall of said tubular member also having an inner surface, and further in which the step of applying a force is further characterized as applying a compressive force sufficient to impart a contour on both said inner surface and said outer surface.

19. The method of claim 12 in which the step of applying the compressive force is performed with a blunt implement that applies a force of 150 gm.

20. The method of claim 12 in which the step of applying a compressive force is carried out to only a portion of the length of the tubular member to provide a second region adjacent to the region to which the compressive force is applied such that the second region includes a uniform surface.

21. The method of claim 12 in which the step of applying a compressive force is carried out with a blunt implement.

* * * * *

UNITED STATES PATENT AND TRADEMARK OFFICE
CERTIFICATE OF CORRECTION

PATENT NO. : 5,507,995
DATED : April 16, 1996
INVENTOR(S) : Cyril J. Schweich, Jr. et al.

It is certified that error appears in the above-indentified patent and that said Letters Patent is hereby corrected as shown below:

<u>On the Title Page</u>

Under the heading "OTHER PUBLICATIONS", line 8, delete "uSCI" and substitute --USCI--.

<u>In the Claims</u>

In claim 1, line 5, delete "," and substitute --;--.

In claim 6, line 5, after "force" insert --.--.

Signed and Sealed this

Second Day of September, 1997

Attest:

BRUCE LEHMAN

Attesting Officer    Commissioner of Patents and Trademarks